United States Patent

Groenke

[11] Patent Number: 6,115,638
[45] Date of Patent: Sep. 5, 2000

[54] MEDICAL ELECTRODE WITH CONDUCTIVE RELEASE LINER

[75] Inventor: Allen W. Groenke, Bloomington, Minn.

[73] Assignee: SurVivaLink Corporation, Minneapolis, Minn.

[21] Appl. No.: 09/152,565

[22] Filed: Sep. 14, 1998

Related U.S. Application Data

[60] Provisional application No. 60/084,009, May 4, 1998.

[51] Int. Cl.[7] .................................. A61N 1/04; A61B 5/04
[52] U.S. Cl. .......................... 607/142; 607/152; 600/392
[58] Field of Search .................................... 607/142, 152; 600/391–393

[56] References Cited

U.S. PATENT DOCUMENTS

| | | |
|---|---|---|
| D. 243,717 | 3/1977 | Edmark et al. . |
| 2,590,876 | 4/1952 | Landauer . |
| 3,602,216 | 8/1971 | Moe, Jr. . |
| 3,685,645 | 8/1972 | Kawaguchi . |
| 3,698,549 | 10/1972 | Glassman . |
| 3,701,346 | 10/1972 | Patrick, Jr. et al. . |
| 3,805,769 | 4/1974 | Sessions . |
| 3,834,373 | 9/1974 | Sato . |
| 3,868,946 | 3/1975 | Hurley . |
| 3,961,623 | 6/1976 | Milani et al. . |
| 4,034,854 | 7/1977 | Bevilacqua . |
| 4,040,412 | 8/1977 | Sato . |
| 4,082,086 | 4/1978 | Page et al. . |
| 4,092,985 | 6/1978 | Kaufman . |
| 4,176,746 | 12/1979 | Kooi . |
| 4,353,373 | 10/1982 | Sessions et al. .................... 600/392 |
| 4,362,165 | 12/1982 | Carmon et al. . |
| 4,365,634 | 12/1982 | Bare et al. . |
| 4,423,732 | 1/1984 | Tarjan et al. . |
| 4,439,810 | 3/1984 | Shimada et al. . |
| 4,487,313 | 12/1984 | Repik et al. . |
| 4,494,552 | 1/1985 | Heath . |
| 4,522,211 | 6/1985 | Bare et al. . |
| 4,543,958 | 10/1985 | Cartmell . |
| 4,653,501 | 3/1987 | Cartmell et al. . |
| 4,777,954 | 10/1988 | Keusch et al. . |

(List continued on next page.)

FOREIGN PATENT DOCUMENTS

| | | |
|---|---|---|
| 2483215 | 6/1981 | France . |
| 94/27674 | 12/1994 | WIPO . |

Primary Examiner—Carl H. Layno
Attorney, Agent, or Firm—Patterson & Keough, P.A.

[57] ABSTRACT

An electrode system includes a release liner separating a pair of electrodes. The release liner includes a first portion having electrically conductive and non-stick characteristics and a second portion having electrically non-conductive and non-stick characteristics. An electrically conductive portion of the electrode is disposed over the first portion while an adhesive only, electrically non-conductive portion of the electrode is disposed over the second portion. The release liner includes a pair of electrically non-conductive sheets and an electrically conductive sheet interposed between the non-conductive sheets. The non-conductive sheets include an aperture to expose a portion of the conductive sheet for providing electrical conductivity between the pair of electrodes.

29 Claims, 4 Drawing Sheets

U.S. PATENT DOCUMENTS

| | | |
|---|---|---|
| 4,779,630 | 10/1988 | Scharnberg et al. . |
| 4,798,208 | 1/1989 | Faasse, Jr. . |
| 4,838,273 | 6/1989 | Cartmell . |
| 4,852,571 | 8/1989 | Gadsby et al. . |
| 4,978,007 | 12/1990 | Jacobs et al. . |
| 4,979,517 | 12/1990 | Grossman et al. . |
| 5,123,423 | 6/1992 | Scharnberg .............................. 607/152 |
| 5,148,805 | 9/1992 | Scharnberg . |
| 5,150,708 | 9/1992 | Brooks . |
| 5,161,539 | 11/1992 | Evans et al. . |
| 5,184,620 | 2/1993 | Cudahy et al. . |
| 5,191,886 | 3/1993 | Paeth et al. . |
| 5,203,330 | 4/1993 | Schaefer et al. . |
| 5,255,677 | 10/1993 | Schaefer et al. . |
| 5,275,572 | 1/1994 | Ungs et al. . |
| 5,309,909 | 5/1994 | Gadsby et al. . |
| 5,330,526 | 7/1994 | Fincke et al. . |
| 5,341,806 | 8/1994 | Gadsby et al. . |
| 5,354,321 | 10/1994 | Berger . |
| 5,402,884 | 4/1995 | Gilman et al. . |
| 5,431,688 | 7/1995 | Freeman . |
| 5,456,710 | 10/1995 | Gadsby . |
| 5,462,157 | 10/1995 | Freeman et al. . |
| 5,466,217 | 11/1995 | Myers et al. . |
| 5,466,244 | 11/1995 | Morgan . |
| 5,520,683 | 5/1996 | Subramaniam et al. . |
| 5,562,710 | 10/1996 | Olsen et al. . |
| 5,579,919 | 12/1996 | Gilman et al. . |
| 5,591,213 | 1/1997 | Morgan . |
| 5,617,853 | 4/1997 | Morgan . |
| 5,645,571 | 7/1997 | Olson et al. . |
| 5,650,750 | 7/1997 | Leyde et al. . |
| 5,697,955 | 12/1997 | Stolte . |
| 5,817,151 | 10/1998 | Olson et al. . |
| 5,850,920 | 12/1998 | Gilman et al. . |
| 5,974,344 | 10/1999 | Shoemaker, II ........................ 607/152 |

MEDICAL ELECTRODE WITH CONDUCTIVE RELEASE LINER

RELATED APPLICATIONS

The present application claims the benefit of U.S. Provisional Application Ser. No. 60/084,009, filed May 4, 1998 and incorporated herein in its entirety by reference.

BACKGROUND OF THE INVENTION

The present invention relates generally to medical electrodes. In particular the present invention relates to medical electrodes for automated external defibrillators (AEDs).

Automated external defibrillators (AED) are used by first responders such as police officers, firefighters and emergency medical technicians (EMTs) to resuscitate cardiac arrest patients. Studies have shown that the chances of successfully resuscitating the patient decreases approximately ten percent per minute following cardiac arrest. For this reason, an operator must be able to quickly perform the steps necessary to apply electrodes to patient and deliver a rescue shock. Additionally, it is critical that the AEDs carried by the rescuers be fully operational at all times.

To insure AED readiness, the latest AEDs, such as those available from SurVivaLink Corporation of Minneapolis, Minn., have the ability to perform self-tests on a daily and weekly basis, as well as just prior to and just after, a rescue attempt with the AED. One AED self-test system is disclosed in U.S. Pat. No. 5,645,571, which is hereby incorporated by reference in its entirety. One of the key components of the AED is the pair of electrodes that are placed on the patient to apply the defibrillation shock. Accordingly, the self-test insures, among other things, that: (1) the electrodes are properly connected to the AED; (2) a conductive adhesive on the electrodes has not dried out; and (3) the AED is properly charged and capable of applying a shock through the electrodes. In order for the self-test feature to function properly, the packaging in which the electrodes are stored must provide a conductive path from one electrode to another electrode, and the electrodes must be testable without being removed from their sealed package. Maintaining electrodes in an operable state (through the aid of sealed packaging) for long periods of time is necessary due to the long shelf-storage expectancy of an AED prior to its use in an emergency.

Another goal of the rescue community is AED use with minimal training, and with little or no time wasted in applying the AED despite the lack of training. Typical rescuers who use the AEDs do not have extensive medical backgrounds. For this reason, the electronic packaging ideally will provide timely instructions to the rescuer. The electrodes must be easy to use and virtually foolproof in application. For example, the electrodes must also be easily removed from their sealed packaging for application to the patient. Moreover, once the sealed packaging is opened, the conductive self-adhesive portion of the electrodes must be protected from contaminants and against inadvertent adherence to objects other than the patient.

Finally, the placement of AEDs in the hands of First Responders such as police, nurses, school officials, etc. is highly dependent on reducing the cost of obtaining and using an AED. Accordingly, minimizing the cost of components, such as electrodes and their packaging is important.

SUMMARY OF THE INVENTION

An electrode system of the present invention includes a release liner for separating a pair of electrodes. The release liner reduces the cost of the electrode system while improving the electrodes ease-of-application, longevity, and self-test capabilities.

The inventive release liner of the electrode system includes a first portion having electrically conductive and non-stick characteristics and a second portion having electrically non-conductive and non-stick characteristics. An electrically conductive portion of the electrode is disposed over the first portion while an adhesive only, electrically non-conductive portion of the electrode is disposed over the second portion. The pair of electrodes are placed on opposite sides of the release liner. The release liner preferably includes a pair of electrically non-conductive sheets and an electrically conductive sheet interposed between the non-conductive sheets. The non-conductive sheets include an aperture to expose a portion of the conductive sheet for providing electrical conductivity between the pair of electrodes.

The release liner optimizes electrode packaging factors such as the peel force required to remove an electrode from the release liner and the electrical conductivity/resistivity between the electrodes via the release liner. The release liner is fabricated with low-cost, readily available materials which are manufactured in high volumes. Finally, the construction of the release liner facilitates ease-of-use through a display-ready construction.

DETAILED DESCRIPTION OF THE DRAWINGS

Figure 1A:
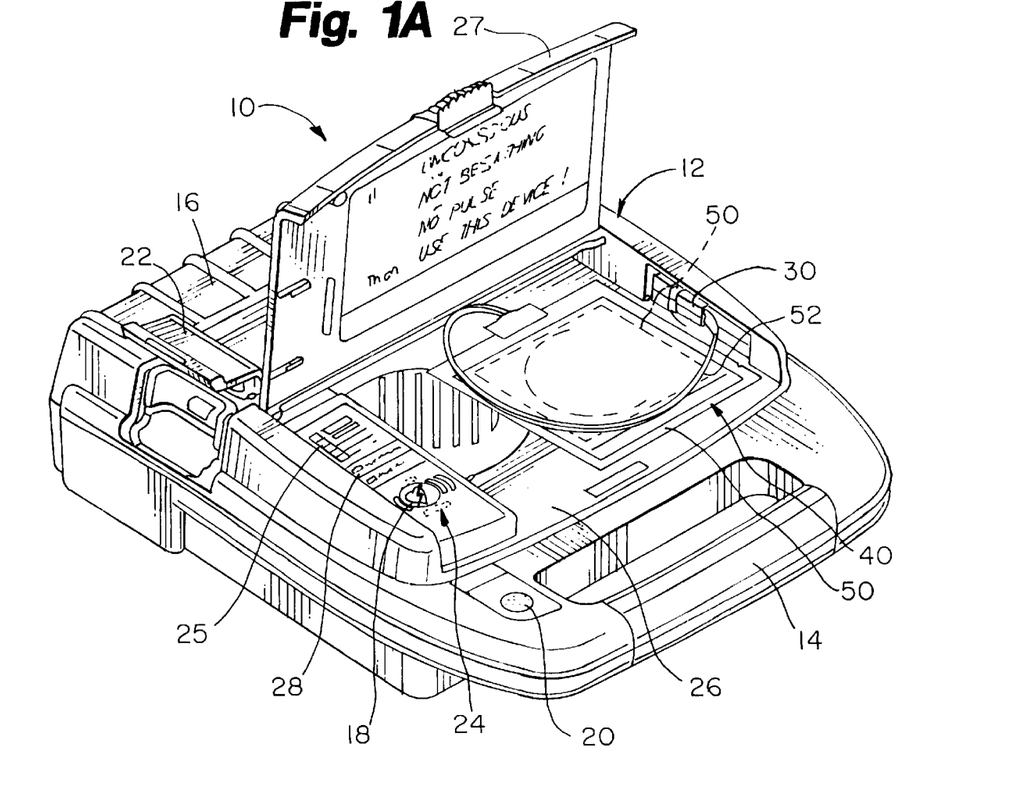
FIG. 1A is a perspective view of an automated external defibrillator (AED) for use with the present invention.

An AED for use with the present invention is shown generally at 10 in FIG. 1. AED 10 is capable of monitoring a patient's cardiac rhythm, detecting cardiac defibrillation by comparing the monitored cardiac rhythm to nominal values, and delivering a series of therapeutic defibrillation shocks if defibrillation is detected.

AED 10 includes case 12 with carrying handle 14 and battery pack 16, which is removably disposed within a battery compartment (not shown) of case 12. Visual maintenance indicator 20 and data access door 22 are located on the outside of case 12 to facilitate access by the operator. Case 12 also defines panel 24 and electrode compartment 26 in a top portion thereof. Panel 24 includes illuminable resume/rescue switch 18 and diagnostic display panel 25 with "Electrodes" indicator light 28. Panel 24 and electrode compartment 26 are enclosed by selectively closeable lid 27.

Electrode compartment 26 contains electrode connector 30 and electrode pouch 40, which hermetically encloses a pair of electrodes 50 in a sealed package. Electrodes 50 are removably connected to electrode connector 30 by leads 52. Electrodes 50 are attached to a patient prior to a rescue intervention procedure with AED 10.

AED 10 also includes a digital microprocessor-based electrical control system (not shown) for controlling overall operation of AED 10 and for delivering a defibrillation shock pulse through electrodes 50 via electrode connector 32 and leads 52. The electrical control system further includes an impedance measuring circuit for testing the interconnection and operability of electrodes 50 to detect several errors. For example, if the conductive adhesive on electrodes 50 is too dry, or if electrodes 50 are not properly connected to electrode connector 32, a relatively high impedance (e.g., greater than about 20 ohms) will be present across electrode connector 32. However, when fresh electrodes 50 are properly packaged, the impedance across electrode connector 32 will be between about 2 and 10 ohms.

To insure operable electrodes, an electrode self-test is conducted (e.g., daily, weekly, or upon opening or closing lid 27) in which the interconnection and operability of electrodes 50 are checked with the impedance measuring circuit. If electrodes 50 are missing or unplugged from connector 30, if electrodes 50 are damaged, or if the conductive hydrogel adhesive on electrodes 50 is too dry, the control system of AED 10 will illuminate "Electrodes" indicator light 28 on diagnostic display panel 25.

Figures 1B, 1C:
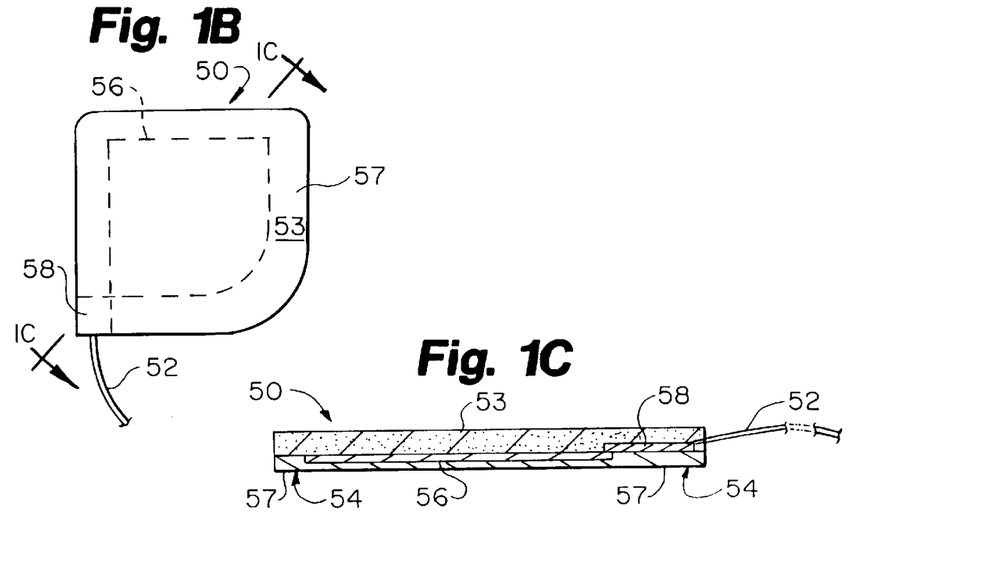
FIG. 1B is a plan view of an electrode pad for use with the present invention.
FIG. 1C is a sectional view of FIG. 1B taken along lines 1C—1C.

As shown in FIGS. 1B and 1C, electrode 50 includes flexible adhesive-coated backing layer 53 (preferably a polymeric foam), and patient-engaging layer 54 which overlays backing layer 53. Patient-engaging layer 54 is preferably a hydrogel material which has adhesive properties and which is electrically-conductive. Hydrogel adhesive of this type is commercially available from Lectec Corporation of Minnetonka, Minn. and Tyco International, Ltd. of Hamilton, Bermuda. Current-disbursing flexible conductive portion 56 is preferably located between backing layer 53 and patient-engaging layer 54. Conductive portion 56, as shown, need not be the same size as backing layer 53 and is preferably a homogeneous, solid, thinly deposited metallic substance, or a conductive ink. Insulated lead wires 52 extend from electrode 50 and have an end electrically connected to conductive portion 56 via conductive terminal 58. As shown in FIGS. 1B–1C, an adhesive-coated border 57 is formed by a portion of adhesive-coated backing layer 53. This border 57 extends about conductive portion 56 and patient-engaging layer 54. Further examples of electrode pad construction for use with an AED 10 and with the present invention are described and shown in U.S. Pat. Nos. 5,697,955; 5,579,919; and 5,402,884, all commonly assigned to the assignee of the present invention, and all of which are hereby incorporated by reference.

An improved electrode system of the present invention for use with AED 10 is illustrated generally at 70 in FIGS. 2A–2E. Electrode system 70 includes electrode release liner 71 having conductive sheet 72 sandwiched between a pair of non-stick sheets 74A and 74B. Release liner 71 further includes side edges 76 and ends 78. Non-stick sheets 74A and 74B are preferably thin, flexible, members and include body portion 80, tabs 82A and 82B, respectively, and single aperture 86. Conductor sheet 72 is also a thin, flexible member which may include optional holes 92 and welding holes 94. When assembled, release liner 71 includes welding lines 96 that extend along side edges 76 with welding spots 98 formed between sheets 74A, 74B within holes 94 of conductive sheet 72.

Figure 2A:
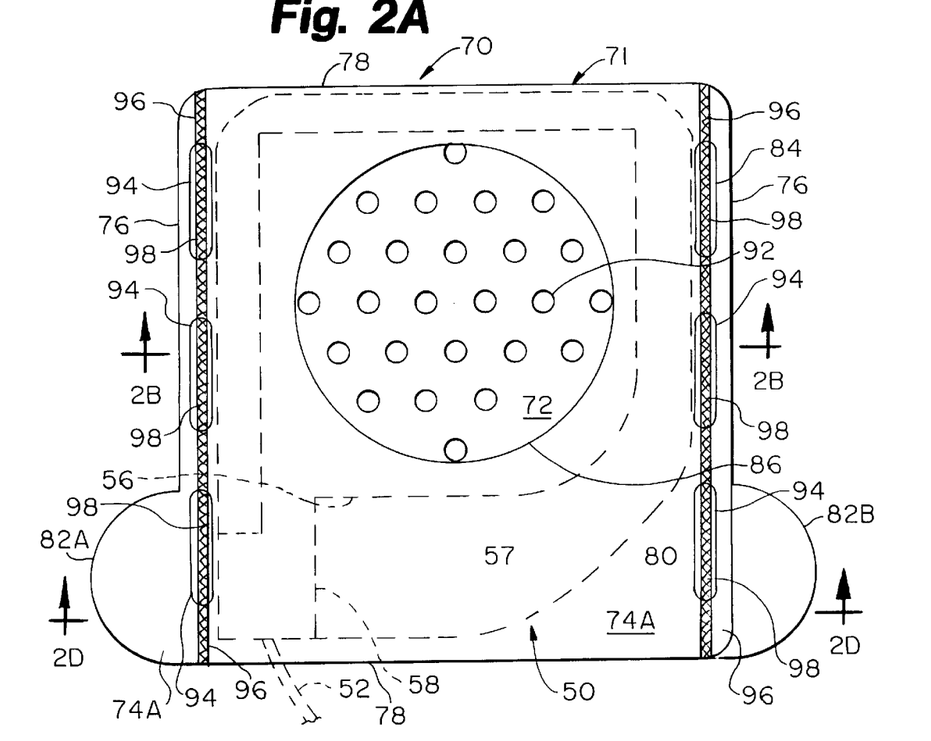
FIG. 2A is a plan view of a release liner of the present invention.
Figures 2B, 2C, 2D:
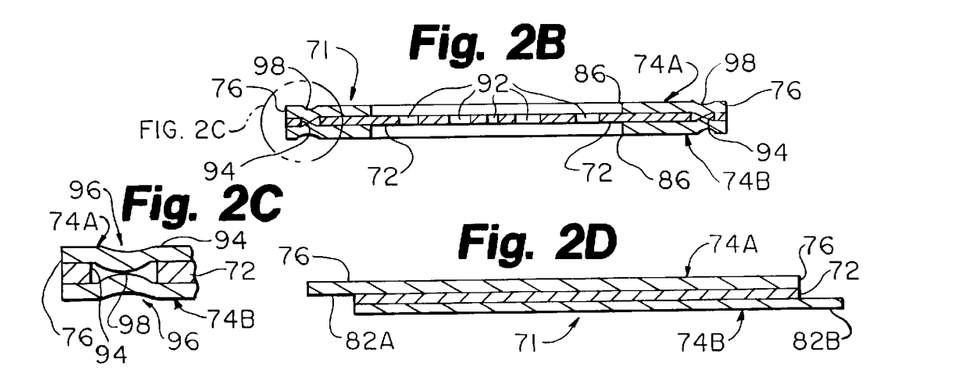
FIG. 2B is a sectional view of the release liner of FIG. 2A as taken along lines 2B—2B.
FIG. 2C is an enlarged sectional view of a portion of FIG. 2B.
FIG. 2D is a sectional view of the release liner of FIG. 2A as taken along lines 2D—2D.

FIG. 2B is a cross sectional view of FIG. 2A taken along lines 2B—2B. FIG. 2B illustrates conductive sheet 72 sandwiched between the pair of non-conductive sheets 74A and 74B. In FIG. 2B, the thicknesses of sheets 72 and 74A, 74B are exaggerated for illustrative purposes. In reality, sheets 74A, 74B are so thin (e.g., 0.0029 inches) that the transition at aperture 86 between sheet 72 and sheets 74A, 74B is substantially flat and does not present a discontinuity or raised surface.

As shown, aperture 86 of non-stick sheets 74A and 74B define a region in 215 which conductive sheet 72 (with optional holes 92 formed therein) is the only layer forming that portion of the release liner 71. In addition, FIG. 2B illustrates welding lines 96, particularly including welding spots 98. As further shown in FIG. 2C, welding spots 98 are formed when non-stick sheet 74A is welded to non-stick sheet 74B in a region of conductive sheet 72 defining hole 94. This construction yields a high weld strength since a stronger weld occurs between sheets 74A, 74B, made of the same first material (further discussed below) than when a weld is made with conductive sheet 72 (made of a different second material) extending between sheets 74A, 74B.

FIG. 2D is a cross-sectional view of release liner 71, taken along lines 2D—2D of FIG. 2A. In this view, conductive sheet 72 is sandwiched between layers 74A and 74B with tab 82A of sheet 74A extending laterally outward from release liner 71 on one side edge 76 and tab 82B extending laterally outward from an opposite side edge 76 of release liner 71. Tabs 82A and 82B facilitate removal of electrodes 50 from release liner 71 by providing rescuers with convenient locations to grasp release liner 71 while peeling off electrodes 50.

In FIG. 2A, electrode pad 50 is shown in phantom as placed onto release liner 71. Electrode pad 50 has the features of electrode 50 shown in FIGS. 1B–1C, and includes conductive portion 56, adhesive border 57, conductive terminal 58, and electrical leads 52.

Figure 2E:
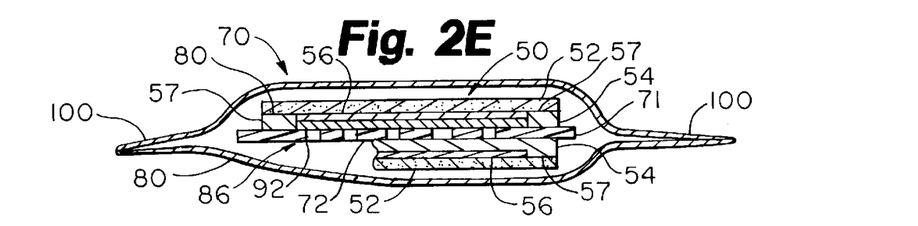
FIG. 2E is a sectional view of a pair of electrodes disposed on a release liner of the present invention within a sealed package.

FIG. 2E is a cross-sectional view of electrode system 70 with a pair of electrodes 50 placed on release liner 71 within sealed package 100. For illustrative purposes, the bottom electrode 50 is shown with a portion broken away, and release liner 71 is simplified into a single thin sheet. Release liner 71 is configured for placing electrode pad 50 on at least one, and preferably both sides of release liner 71. Electrode pad 50 is placed thereon so that patient-engaging layer 54 of electrode pad 50 is disposed over and in direct electrical contact with aperture 86 of release liner 71. This arrangement establishes electrical connectivity, via conductive sheet 72, between conductive portion 56 of an electrode pad 50 on one side of the release liner 71 with conductive portion 56 of another electrode pad 50 on an opposite side of release liner 71. Optional holes 92 in conductor sheet 72 further establish electrical connection between the conductive portions 56 of the electrode pads 50 on opposite sides of the release liner 71. Optional holes 92 permit direct contact between the electrically conductive patient-engaging layer 54 of each of the electrode pads 50. In addition, adhesive border 57 of the electrode pad 50 is disposed over non-stick body 80 of release liner sheets 74A, 74B without contacting conductive sheet 72 within aperture 86.

Conductive sheet 72 is preferably a polyethylene material loaded with carbon particles to render it conductive. Sheet 72 is preferably a 4-mil plastic film which can be obtained from 3M Company of St. Paul, Minn., as Model 1704, or otherwise known as a Velostat™ Electrically-Conductive Film. The electrically-conductive polyethylene material is widely known as polyethylene film used for static control, and rolls of this material may be readily purchased at low cost. Other examples of suitable materials for conductive sheet 72 include a foil made from a conductive metal such as nickel, stainless steel, tin, or aluminum.

Non-stick sheets 74A and 74B are preferably made of a polyester material also available from 3M Company of St. Paul, Minn., as Model 9956, Medical Release Liner. This polyester film is fluropolymer treated on one side to provide non-stick characteristics. Of course, other thermoplastic films could be used such as polyethylene and/or polypropylene materials treated with release agents such as silicon or fluropolymers. Sheets 74A, 74B are preferably transparent, although they can also be translucent or opaque.

As noted above, conductor sheet 72 is secured between non-stick sheets 74A and 74B by welding along welding lines 96. Welding the sheets together permits construction of release liner 71 without the use of a transfer adhesive between non-stick sheets 74A, 74B and conductive sheet 72. This feature results in a significant cost savings due to the expensive nature of the transfer adhesive. This welding construction is accentuated by the use of holes 94 in conductive sheet 72 which permit direct welding between non-stick sheets 74A and 74B as highlighted in FIG. 2C. This results in a much stronger bond due to the superior welding characteristics of direct contact between non-stick sheets 74A, 74B (polyester-to-polyester) as compared to the welding characteristics of the combination of conductive sheet 72 between non-stick sheets 74A and 74B (polyester-to-polyethylene).

Various welding techniques may be used to secure sheets 72, and 74A, 74B. For example, suitable welding techniques include methods of using electromagnetic energy to weld, such as radio frequency energy, and methods of using friction to heat the material, such as ultrasonic welding. In a preferred embodiment, thermal welding techniques are used to weld layered sheets 72, 74A and 74B together. In this method, an electrical heating element is used to guarantee the heat required for welding.

Patient-engaging layer 54 of electrode 50 shown in FIG. 1C, preferably comprises a hydrogel material which is electrically conductive and also has adhesive properties, thereby permitting the patient-engaging layer 54 to form an electrical connection with the body and to adhere the electrode to the patient's skin. Adhesive-coated border portion 57 preferably includes an acrylic adhesive to provide additional adhesion between electrodes 50 and the patient's skin.

When electrode pad 50 is placed on release liner 71, the aggressive acrylic adhesive is permitted only to contact non-stick sheets 74A and 74B while the hydrogel material constituting patient-engaging layer 54 is permitted to contact conductive sheet 72 via aperture 86 of non-stick sheets 74A and 74B.

If the acrylic adhesive on border portion 57 were allowed to contact conductive sheet 72, it would bond aggressively, making electrodes 50 difficult to remove from release liner 71. The materials used to fabricate non-stick sheets 74A and 74B are elected so that both hydrogel adhesive and acrylic adhesive will only bond lightly to non-stick sheets 74A and 74B. The result is that electrodes 50 can be easily peeled off release liner 71.

Finally, optional holes 92 in conductive polyethylene sheet 72 may be used to reduce electrical impedance between electrodes 50 on opposite sides of release liner 71. Optional holes 92 must be small and few in number to avoid significantly increasing the peel force required to remove electrodes 50 from release liner 71.

In operation, as shown in FIG. 2E, an electrode pad 50 is placed on each side of release liner 71. Release liner 71 covers patient-engaging layer 54 and adhesive border portion 57 of electrode pad 50 until ready for use. This liner prevents patient-engaging layer 54 and adhesive border portion 57 from collecting contaminants. Liner 71 also prevents adherence of the electrode pad to any other object. Of course, removably securing electrodes 50 on each side of release liner 71 permits electrical conductivity between electrodes 50 for performing the electrode self-tests described above. Non-stick sheets 74A and 74B permit easy peeling removal of electrodes 50 from release liner 71 when required for application of electrodes 50 to a patient.

Figure 3A:
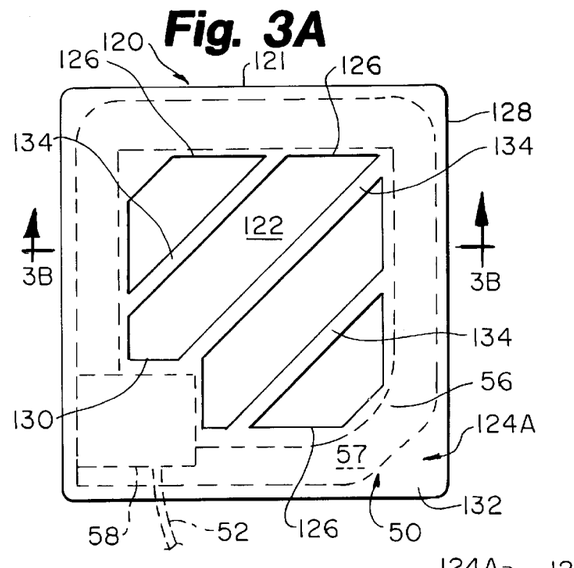
FIG. 3A is a plan view of a release liner of the present invention.
Figure 3B:
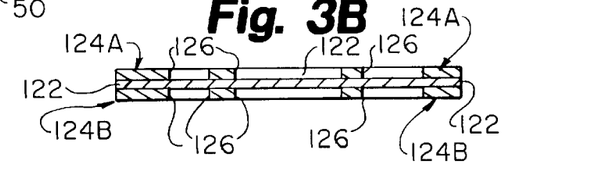
FIG. 3B is a sectional view of the release liner of FIG. 3A as taken along lines 3B—3B.

In another embodiment, shown in FIGS. 3A and 3B, electrode system 120 of the present invention includes release liner 121. Release liner 121 includes conductive sheet 122 sandwiched between a pair of non-stick sheets 124A and 124B. Non-stick sheets 124A and 124B include patterned apertures 126 to expose conductive sheet 122 therethrough. A pattern of apertures 126 form non-stick striping 134 between apertures 126. In addition, the patterned apertures 126 are formed generally in the shape of a rectangle with a single corner recess 130. This arrangement results in a non-stick border 132. As shown in phantom, electrode 50 can be placed over release liner 121 so that adhesive-coated border portion 57 of electrode pad 50 is disposed over non-stick border 132 of release liner 121 while conductive portion 56 of electrode pad 50 is disposed generally over patterned recesses 126, i.e., over the exposed portions of conductive sheet 122. Moreover, electrode terminal 58 is conveniently located over the non-conductive, rectangular-shaped patterned corner recess 130 of release liner 121.

Non-stick striping 134 is comprised of multiple stripes 134 that extend generally parallel to one another along a direction in which electrode pad 50 is peeled off release liner 121. Providing non-stick striping 134 in parallel along this direction reduces the peeling force necessary to remove electrode pad 50 from release liner 121.

Figure 4A:
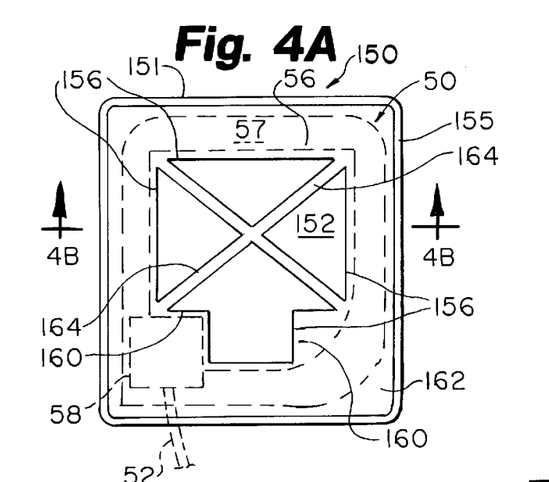
FIG. 4A is a plan view of a release liner of the present invention.
Figure 4B:
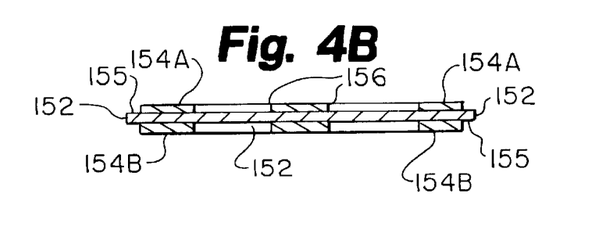
FIG. 4B is a sectional view of the release liner of FIG. 4A as taken along lines 4B—4B.

In another embodiment, shown in FIGS. 4A and 4B, electrode system 150 of the present invention includes release liner 151, having conductive sheet 152 sandwiched between a pair of non-stick sheets 154A and 154B. Non-stick sheets 154A and 154B include patterned holes 156 which permit exposure of conductive sheet 152 therethrough. Patterned holes 156 are arranged generally in the form of a rectangle comprised of multiple triangular sections having at least one of their vertices opposed to each other. The arrangement of patterned holes 156 creates non-stick striping 164 as well as corner, non-stick rectangular-shaped portions 160. The remainder of non-stick sheets 154A and 154B define non-stick border 162.

With this arrangement, conductive portion 56 of electrode pad 50 is disposed over conductive sheet portion 152 exposed through patterned holes 156 of release liner 151. In addition, adhesive-coated border portion 57 of electrode pad 50 is disposed over non-stick border 162. Corner recesses 160 are shaped to accommodate electrode pad terminal 58.

Unlike the embodiment shown in FIGS. 2A–2F, conductive sheets 122 and 152 do not include optional holes, and therefore do not permit direct contact of hydrogel materials (on patient-engaging layer 54 on electrode pads 50) on opposite sides of release liner 121 or 151 therethrough as in the embodiment of FIG. 2A. Accordingly, the embodiment FIGS. 3A and 4A prevents the hydrogel material on layer 54 on one electrode 50 from adhering strongly to the hydrogel material on layer 54 on the other electrode 50. Electrical conductivity between electrodes is still maintained since sheets 122 or 152 are electrically conductive. The lack of optional holes 92 reduces the peeling force required to remove electrodes 50 from release liner 121 or 151. However, the lack of optional holes 92 also increases the electrical impedance between electrodes 50.

Both the embodiments of FIG. 3A and FIG. 4A have a similar construction in that both include conductive sheet (122 or 152) formed of a polyethylene film loaded with carbon particles to provide its conductive characteristics. Non-stick sheets 124A, 124B and 154A, 154B are preferably a polyester film treated on an outer side of the non-stick sheet with a release agent such as fluropolymer or silicone. A transfer adhesive is placed on an inner side of the sheet (124A, 124B and 154A, 154B) for bonding the adhesive side of each non-stick sheet to a conductive sheet (122 or 152). A suitable transfer adhesive is commercially available from 3M Company of St. Paul, Minn., identified as model 1524. When transfer adhesive is used, non-stick sheets 124A, 124B and 154A, 154B may be made of a non-thermoplastic material such as paper treated with a release agent. Non-stick sheets 124A, 124B and 154A, 154B may also be made of thermoplastic materials such as polyester, polyethylene or polypropylene.

While a preferred embodiment of the present invention is for use with AEDs, the electrode system of the present invention can be used for many other medical procedures such as EKG, EEG, EMG, ESU, TENS etc.

Of course, various features from each of the embodiments can be combined and/or modified as necessary. For example, the greater the area of the electrode hydrogel, which is allowed to contact the conductive sheet (such as 72, 122 or 152), the lower the electrical impedance. However, this increased contact will increase the peel force required to remove the electrodes from the release liner. In addition, the electrical impedance can be further reduced by placing holes in the exposed portion of conductive sheet (72, 122 or 152), to allow direct contact of the hydrogel between the electrodes. This arrangement also increases the peel force required to remove the electrodes from the release liner.

Finally, the multiple sheet construction of release liner (71, 121 or 151) facilitates placement of important, instruction labeling in a manner that does not interfere with the non-stick/electrically-conductive interface between the electrode pads and the release liner.

Figure 5:
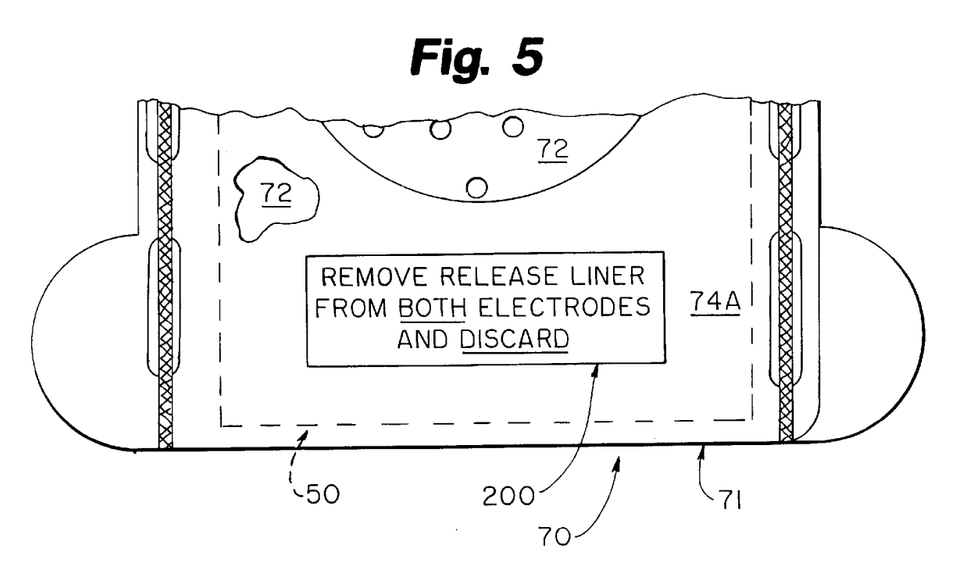
FIG. 5 is an enlarged plan view of a portion of a release liner of the present invention.

As shown in FIG. 5, release liner 71 includes instruction label 200 secured thereon either on inner surface of transparent sheet 74A or on the surface of sheet 72. When an electrode pad 50 is placed on liner 71, label 200 will be hidden. However, when electrode pad 50 is removed for application to a patient, label 200 becomes visible to provide the operator with a timely reminder. Instruction label 200 reminds the operator to remove both electrodes 50 from the release liner 71. This instruction is intended to prevent application of an electrode to the patient's chest while release liner 71 is still adhered to it. While seemingly simplistic, the multiple sheet construction which facilitates this labeling is significant since labeling on an outer surface of a single sheet release liner can interfere with the non-stick/electrically-conductive interface between the electrode pads and the release liner.

The combination of multi-sheet construction and the location of instruction labeling on the release liner is also significant since the labeling provides an instructive reminder of the exact point in time when it is needed. The operator of an AED will most likely be a first responder, such as a firefighter or police officer. These operators typically have little medical background and do not routinely perform defibrillation. Clear and timely instructions are critical when performing a rescue in a high-stress, emergency situation.

The information in label 200 also can be printed directly onto the inner surface of transparent sheet 74A or on the surface of sheet 72.

Although the present invention has been described with reference to preferred embodiments, those skilled in the art will recognized that changes can be made in form and detail without departing from the spirit and scope of the invention.

What is claimed is:

1. An electrode release liner comprising:
a pair of electrically non-conductive sheets;
an electrically conductive sheet interposed between the non-conductive sheets, each nonconductive sheet having an opening exposing a portion of the electrically conductive sheet.

2. The liner of claim 1 wherein the conductive sheet has at least one aperture in the exposed portion.

3. The liner of claim 1 wherein conductive sheet and nonconductive sheets have thermally welded joints.

4. The liner of claim 3, wherein the joints extend along opposite edges of the liner.

5. The liner of claim 3, wherein the conductive sheet includes at least one aperture defined along each side edge of the conductive sheet and a portion of each of the non-conductive sheets extends over the side edge aperture, and the non-conductive sheets are secured together within the side edge aperture of the conductive sheet.

6. The liner of claim 5, wherein the conductive sheets are secured together in a thermally welded joint within the side edge aperture.

7. The release liner of claim 1 wherein each non-conductive sheet has a non-stick side and an adhesive side with the adhesive side bonded adhesively to the conductive sheet.

8. The release liner of claim 1 wherein the non-conductive sheet is made from at least one of a polyester film, a polyethylene film, and a polypropylene film.

9. The release liner of claim 8, wherein the non-conductive sheet includes at least one of a fluropolymer component and a silicone component.

10. The release liner of claim 1 wherein the conductive sheet is made from at least one of a polyethylene film, and a conductive metal foil.

11. The release liner of claim 10, wherein the metal is nickel.

12. The release liner of claim 1 wherein the non-conductive sheets are transparent.

13. The release liner of claim 10, wherein the non-conductive sheets and the conductive sheet have a non-stick surface.

14. The release liner of claim 13, wherein the non-stick surface of the non-conductive sheets have a greater releasability characteristic than the non-stick surface of the conductive sheet.

15. An electrode system comprising:
a pair of electrode pads disposed on opposite sides of a release liner, the release liner comprising:
first means for providing electrical conductivity between the electrode pads and releasable attachment of the electrode pads relative to the liner; and
second means for facilitating electrically nonconductive releasable attachment of the electrode pads relative to the liner.

16. The system of claim 15, wherein the first means includes a lesser degree of releasability than the second means.

17. An electrode system comprising:
a pair of electrode pads disposed on opposite sides of a release liner, the release liner comprising:
a first portion being electrical conductive and permitting releasable attachment of the electrode pads relative to the liner; and
a second portion being electrically nonconductive and permitting releasable attachment of the electrode pads relative to the liner.

18. The system of claim 17, wherein the second portion permits a greater degree of releasability than the first portion.

19. An electrode release liner including:
a pair of non-stick, electrically non-conductive sheets, each having an aperture formed therein; and
an electrically conductive sheet interposed between the pair of non-conductive sheets and being exposed through the aperture of the nonconductive sheets, and having a first plurality of holes in the exposed portion, wherein the non-conductive sheets are secured together only along opposed side edges of the conductive sheet.

20. An electrode release liner including:
a pair of electrically non-conductive sheets, each having a plurality of apertures formed therein, each non-conductive sheet having a non-stick side and an adhesive side; and
an aperture-less electrically conductive sheet interposed between the pair of non-conductive sheets and being exposed through the aperture of the non-conductive sheets;
wherein the adhesive side of each the non-conductive sheets is secured to the conductive sheet.

21. An electrode package system comprising:
a releasable liner including:
a pair of non-stick, electrically non-conductive sheets, each having an aperture formed therein;
an electrically conductive sheet interposed between the pair of non-conductive sheets and being exposed through the aperture of the nonconductive sheets;
a pair of electrically active electrode pads having a releasably adhering surface with a nonconductive portion and a conductive portion, each electrode pad disposed on opposite sides of the release liner with the conductive portion in electrical contact with the exposed conductive sheet portion of the release liner.

22. The electrode package system of claim 21, wherein the conductive sheet further includes at least one aperture in the exposed portion.

23. The electrode package system of claim 21, wherein the aperture of the non-conductive sheet includes more than one aperture portions.

24. The electrode package system of claim 23, wherein the aperture portions have elongate shapes and extend generally parallel to one another relative to a first axis, thereby further defining a plurality of non-stick, non-conductive portions of the non-stick, non-conductive sheets extending between the elongate aperture portions and being generally parallel to each other and the elongate aperture portions.

25. The system of claim 23, wherein the aperture portions together generally define a rectangular shape.

26. The system of claim 23, wherein each aperture portion generally defines a triangular shape.

27. The system of claim 26, wherein an elongate non-stick, non-conductive portion of the non-stick, non-conductive sheet extends between each of the triangular shaped portions.

28. The system of claim 23, wherein the aperture portions together generally define a circular shape.

29. The system of claim 21, wherein the non-stick, non-conductive sheet is transparent.

* * * * *